United States Patent [19]

Weilbacher

[11] Patent Number: 4,664,652
[45] Date of Patent: May 12, 1987

[54] WOUND EVACUATOR
[75] Inventor: Eugene E. Weilbacher, New Philadelphia, Ohio
[73] Assignee: Snyder Laboratories, Inc., Dover, Ohio
[21] Appl. No.: 699,364
[22] Filed: Feb. 7, 1985
[51] Int. Cl.⁴ .......................................... A61M 37/00
[52] U.S. Cl. ..................................... 604/133; 604/216; 604/256; 604/324; 128/765; 128/767
[58] Field of Search ................................. 604/131–134, 604/140, 216, 217, 256, 316, 317, 319, 324, 326, 403, 408; 128/760, 765, 767, DIG. 26; 220/202, 366, 367

[56] References Cited

U.S. PATENT DOCUMENTS

| 3,115,138 | 12/1963 | McElvenny | 128/278 |
|---|---|---|---|
| 3,376,868 | 4/1968 | Mondiadis | 128/278 |
| 3,572,340 | 3/1971 | Lloyd | 604/133 |
| 3,742,952 | 7/1973 | Magers | 128/278 |
| 3,871,377 | 3/1975 | Treace | 604/133 |
| 3,900,029 | 8/1975 | Melnick | 604/133 |
| 4,055,179 | 10/1977 | Manschot | 604/322 |
| 4,141,361 | 2/1979 | Snyder | 604/133 |
| 4,310,102 | 1/1982 | Walter | 220/366 |
| 4,347,946 | 9/1982 | Nichols | 604/319 |
| 4,372,921 | 2/1983 | Sanderson | 220/367 |
| 4,376,439 | 3/1983 | Lauterjung | 128/276 |
| 4,578,060 | 3/1986 | Huck | 604/134 |

FOREIGN PATENT DOCUMENTS

| 2504253 | 8/1975 | Fed. Rep. of Germany | 604/317 |
|---|---|---|---|
| 645733 | 11/1950 | United Kingdom | 220/367 |
| 1102994 | 2/1968 | United Kingdom | 604/256 |
| 2144829 | 3/1985 | United Kingdom | 604/317 |

Primary Examiner—Stephen C. Pellegrino
Assistant Examiner—Mark Rooney
Attorney, Agent, or Firm—Paul David Schoenle

[57] ABSTRACT

A wound evacuator comprises a pair of walls which are pushed apart by springs to generate suction in a cavity. A strap coupled to one of the walls includes a plug to close an outlet, a slot cooperating with a peg on the one wall to retain the strap adjacent the one wall and a tab to prevent contact by an individual with the plug upon removal and reinsertion of the plug in the outlet.

5 Claims, 3 Drawing Figures

WOUND EVACUATOR

The present invention relates to a wound evacuator for a patient wherein body fluids are drained from the patient at the location of a wound resulting from surgery. It is common to provide for drainage of wounds subsequent to surgery to decrease healing time and contribute to patient comfort.

In U.S. Pat. No. 3,115,138 (McElvenny et al) issued Dec. 24, 1963, an evacuator is disclosed with end walls biased apart by a plurality of springs. A side wall limits separation between the pair of end walls and cooperates therewith to define a cavity. When the end walls are collapsed toward each other the springs are contracted and the volume of the cavity is also contracted. As the springs bias the end walls apart a suction is created in the cavity to provide for communication of body fluids to the cavity via a suitable tube or tubes disposed within the wound. An inlet is connected to the tube and an outlet receives a plug to confine the suction to the inlet and the tube during drainage.

When the evacuator of the above-mentioned patent is filled with body fluid, the plug is removed to permit drainage of the body fluids from the cavity. Thereafter, the evacuator is again collapsed and the plug reinserted in the outlet to generate suction in the cavity. With both hands used to collapse the evacuator, it is difficult to align the plug with the outlet and insert the latter while at the same time retaining the evacuator in a fully collapsed state. Also, the plug is exposed to the body fluids in the cavity so that the plug is partially covered with body fluids, which can be transmitted to the hands if the plug is grasped for reinsertion in the outlet.

The present invention provides an evacuator with a plug that is disposed in the outlet in a first position for retention therein while also providing a fluid passage to permit venting of the cavity. After the cavity is vented, the plug is easily inserted further in the outlet to close the latter when the plug is in a second position. Moreover, the plug is carried by a strap with at least one tab which acts as a barrier to prevent an individual's fingers from contacting that portion of the plug covered by body fluids.

It is an object of the present invention to provide a wound evacuator with a plug that is easily inserted in an outlet for the evacuator; is compactly coupled to an end wall of the evacuator, and provides for minimal transfer of body fluids to an individual emptying the evacuator.

Turning to the drawings accompanying this specification,

Figure 1:
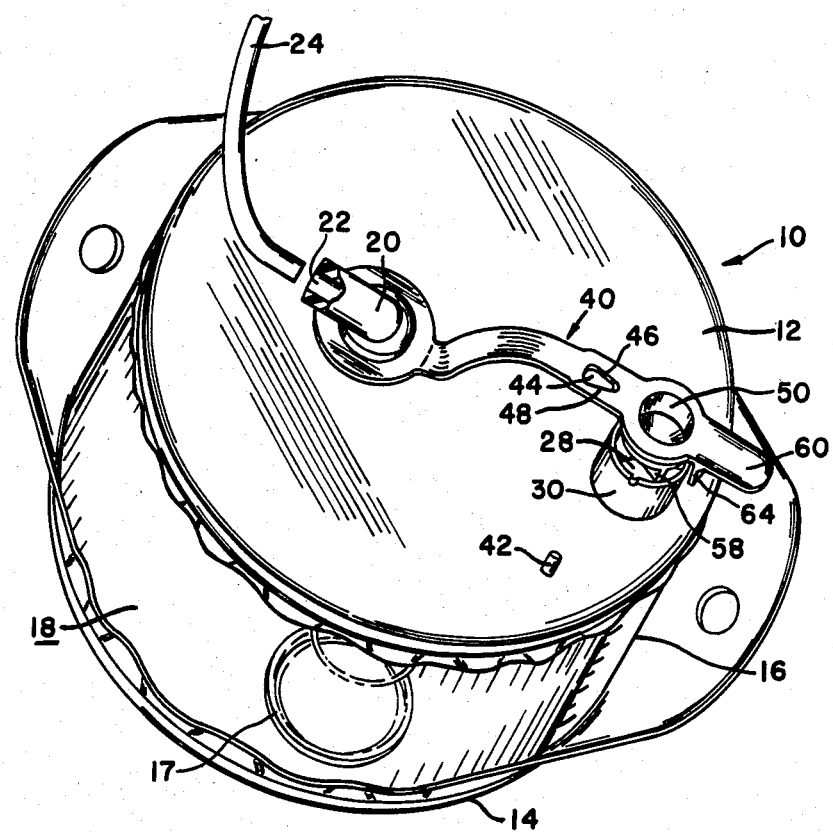
FIG. 1 is a perspective view of the wound evacuator covered by this invention.
Figure 3:
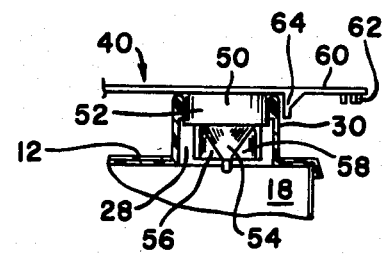
FIG. 3 is a cut-away view of the the top wall with the plug in its fully installed position.

The wound evacuator 10 includes a top wall 12, a bottom wall 14 and a side wall 16 connected to the top wall 12 and the bottom wall 14 to limit separation of the walls and cooperate with the latter to form a cavity 15. Springs 17 or the like are disposed in the cavity 18 to bias the top and bottom walls apart. A fitting 20 is coupled to the top wall 12 so that an opening 22 on the fitting 20 communicates with an inlet leading to the cavity 18 via a one-way check valve (not shown). Suitable tubing 24 is adapted to connect with the fitting 20 and is disposed in communication with the wound which is to be drained. As shown in U.S. Pat. No. 4,141,361, issued to Harold I. Snyder, a tube for a wound evacuator normally connects with a perforated wound tube carrying a surgical needle to permit disposition of the perforated wound tube within a wound. An outlet 28 on the top wall communicates directly with the cavity 18. In order to form the outlet 28 a tubular projection 30 extends outwardly from the top wall 12.

A strap 40 is fixedly connected to the top wall 12 at the location of the fitting 20. The strap is flexible to permit stretching thereof to fit over a peg 42, see FIG. 2, extending outwardly from the top wall 12. The strap 40 includes a slot 44 with tapered edges 46 and 48 facilitating disposition of the strap over the peg 42. The strap 40 includes a plug 50 adapted to fit into the tubular projection 30. The plug 50 is formed with a base 52 defining a first slightly tapered outer surface and a leading end 54 with a second tapered outer surface. Both surfaces are frusto conical in shape with the first outer surface forming a smaller taper than the second outer surface. A pair of flanges 56 and 58 intersect and extend outwardly from the leading end for a purpose to be defined hereinafter. The strap terminates in a finger engaging end portion 60 opposite the fitting 20. A plurality of stubs 62 are provided on the end portion to facilitate gripping the end portion 60. A tab 64 extends from the strap in the same direction as the plug 50 so that a finger engaging the end portion 60 will remain spaced from the plug 50. The tab 64 is adjacent to but spaced from the plug 50.

Figure 2:
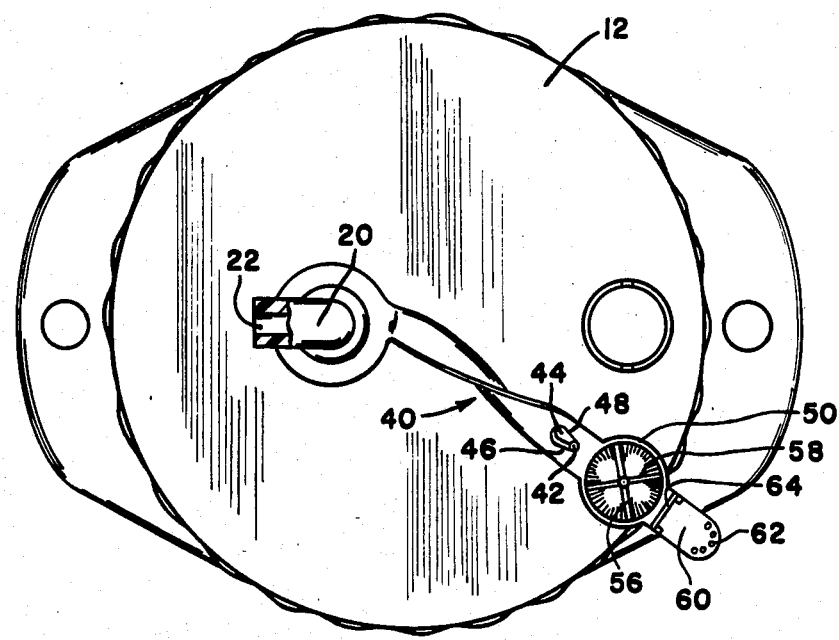
FIG. 2 is a top view of an end wall shown in FIG. 1.

In order to open the outlet 28 and maintain the plug in spaced relation thereto the strap 40 is stretched to align the slot 44 with the peg 42, see FIG. 2. Once the peg is fitted in the slot 44 a restoring force, generated by stretching the strap, tightly engages the strap with the peg 42 to retain the strap 40 and plug 50 in a compact arrangement adjacent the top wall. As shown, the strap is also twisted so that the plug extends away from the top wall. When the wound evacuator is connected to tubing 24 for wound drainage, the strap 40 is separated from the peg by gripping the end portion 60 and stretching the strap away from fitting 20. The strap 40 is then twisted and moved to align the plug 50 with the outlet 28. For convenience the length of the strap between the fitting 20 and the plug 50 is substantially the same length as the distance between the fitting 20 and the outlet 28. The plug 50 is partially fitted in the tubular projection 30, see FIG. 1, so that the pair of flanges 56 and 58 engage the wall of the tubular projection to frictionally retain the plug 50 in alignment with the outlet and define a passage leading to the cavity 18. In order to generate a vacuum or negative pressure in the cavity 18, the top and bottom walls 12 and 14 are pressed together to vent air in the cavity 18 out through the passage around the pair of flanges 56 and 58. Once the top and bottom walls 56 and 58 are disposed adjacent each other, the plug 50 is pressed further into the tubular projection so that the base 52 forms a sealing interface with the tubular projection 30. The plug 50 remains in the tubular projection 30 as a result of friction and because of a pressure differential biasing the plug 50 into the cavity 18. At this time the top and bottom walls are biased apart to create suction in the cavity 18 which initiates flow of body fluids from the wound to the cavity 18.

When the cavity 18 is filled with body fluids and the top and bottom walls are fully separated, an individual is able to grip the end portion 60 of the strap to pull the plug 50 out from the tubular projection 30 and couple the strap 40 to the peg 42 as previously described. With the outlet 28 directed toward a suitable container for the body fluids, the top and bottom walls are pressed together to expell the body fluids from the cavity 18 into the container while the strap 40 and plug 50 are restrained via the peg 42. With the top and bottom walls disposed adjacent each other it is now possible to reposition the plug 50 fully in the tubular projection 30 to initiate suction and drainage of the wound. The one-way check valve in the fitting 20 (not shown) prevents any body fluid from returning to the wound after it is communicated to the cavity.

In view of the foregoing description, it is seen that the strap 40 incorporates several features facilitating operation of the wound evacuator. The slot 44 permits the strap to be compactly stored adjacent the top wall 12. The pair of flanges 56 and 58 permit the plug 50 to be aligned and partially inserted in the outlet 28 to form a passage and facilitate movement to a final fit. The tab 64 prevents an individual from coming in contact with the plug when the latter is covered with body fluids.

I claim:

1. A wound evacuator for extraction of body fluids from a patient via tubing extending between the patient and the wound evacuator, the evacuator including a pair of end walls, a side wall extending between the pair of end walls to sealingly engage the latter, the side wall extending around the periphery of the end walls and cooperating with the pair of end walls to define a cavity, one of the pair of end walls defining a first opening leading to the cavity and a second opening carrying valve means for permitting one way fluid communication between the cavity and the patient, and a strap coupled to the one wall, the strap including a plug adapted to fit in the first opening, the plug including flanges extending outwardly therefrom to engage a wall of the first opening to align the plug with the first opening and releasably retain the plug adjacent the first opening when the pair of end walls are moved together to contract the cavity, the flanges cooperating with the wall of the first opening to form a path when the plug is partially received in the first opening in order to vent the cavity only through the first opening, the plug being fully received in the first opening to close the latter so that a partial vacuum is generated in the cavity as the pair of end walls move away from each other via a spring in order to communicate the body fluid from the patient to the cavity via the second opening, the one wall being provided with a peg extending outwardly therefrom and the strap being provided with a slot, the strap being substantially resilient to stretch slightly in order to align the slot with the peg so that the peg is received in the slot, and the resiliency of the strap maintains the latter tightly engaged with the peg to releasably fasten the strap adjacent the one wall.

2. The wound evacuator of claim 1 in which the plug extends outwardly from the strap away from the one wall when the strap is tightly engaged with the peg.

3. The wound evacuator of claim 1 in which the strap is twisted when in tight engagement with the peg.

4. The wound evacuator of claim 1 in which the peg is spaced from the first opening to retain the strap in spaced relation to the first opening when in tight engagement with the peg.

5. A wound evacuator for extraction of body fluids from a patient via tubing extending between the patient and the wound evacuator, the evacuator comprising a pair of end walls coupled to a side wall which extends around the periphery of the end walls to substantially define a cavity, one of the end walls to substantially define a cavity, one of the end walls including a first opening leading to the cavity and a second opening cooperating with a one-way check valve to provide for communication of the body fluids to the cavity, the one end wall supporting a strap with a plug, the plug cooperating with the first opening to close the latter when body fluids are communicated to the cavity, and the one end wall includes a locking means adapted for repeated cooperation with the strap to releasably fasten the strap adjacent the one end wall in spaced relation to the first opening each time the plug is moved away from the first opening, the strap is substantially resilient to permit deformation and stretching thereof when in cooperation with the locking means and a restoring force generated by the strap during deformation and stretching maintains the strap in cooperation with the locking means, and the locking means comprises a peg, and the strap is provided with a slot which receives the peg when the strap is fastened adjacent the one end wall.

* * * * *